US012680061B2

(12) United States Patent
Donahue et al.

(10) Patent No.: US 12,680,061 B2
(45) Date of Patent: Jul. 14, 2026

(54) GAS PERMEABLE INTRAVAGINAL CULTURE DEVICE

(71) Applicant: REPROHEALTH TECHNOLOGIES, INC., Indianapolis, IN (US)

(72) Inventors: James Donahue, Indianapolis, IN (US); Michael Whitt, San Luis Obispo, CA (US); Katherine Russell, Lebanon, IN (US); Christina Nicole Harrison, San Francisco, CA (US); Sarah Sanders, San Diego, CA (US)

(73) Assignee: Reprohealth Technologies, Inc., Indianapolis, IN (US)

( * ) Notice: Subject to any disclaimer, the term of this patent is extended or adjusted under 35 U.S.C. 154(b) by 1245 days.

(21) Appl. No.: 17/508,165

(22) Filed: Oct. 22, 2021

(65) Prior Publication Data

US 2022/0135920 A1 May 5, 2022

Related U.S. Application Data

(60) Provisional application No. 63/108,817, filed on Nov. 2, 2020.

(51) Int. Cl.
| | |
|---|---|
| *C12M 3/00* | (2006.01) |
| *A61B 17/435* | (2006.01) |
| *C12M 1/00* | (2006.01) |
| *C12M 1/04* | (2006.01) |

(52) U.S. Cl.
CPC ........... *C12M 21/06* (2013.01); *A61B 17/435* (2013.01); *C12M 23/24* (2013.01); *C12M 23/34* (2013.01); *C12M 23/38* (2013.01); *C12M 23/44* (2013.01); *C12M 23/46* (2013.01); *C12M 23/54* (2013.01)

(58) Field of Classification Search
CPC ...... C12M 21/06; C12M 23/24; C12M 23/34; C12M 23/38; C12M 23/44; C12M 23/46; C12M 23/54; A61B 17/435; A61B 2017/00477
USPC ....................................................... 600/33–35
See application file for complete search history.

(56) References Cited

U.S. PATENT DOCUMENTS

| | | | |
|---|---|---|---|
| 4,701,161 | A | 10/1987 | Lenck |
| 4,902,286 | A | 2/1990 | Ranoux |
| 5,084,004 | A | 1/1992 | Ranoux |
| 5,135,865 | A | 8/1992 | Ranoux |
| 5,532,155 | A | 7/1996 | Ranoux |

(Continued)

FOREIGN PATENT DOCUMENTS

RU         2250757 C2      4/2005

OTHER PUBLICATIONS

Misao Fukuda et al., Unexpected low oxygen tension of intravaginal culture, Human Reproduction vol. 11 No. 6 pp. 1293-1295, 1996.

(Continued)

*Primary Examiner* — Sunita Reddy
(74) *Attorney, Agent, or Firm* — E. Victor Indiano; Indiano Law Group LLC

(57) ABSTRACT

An intravaginal culture device includes an outer housing configured for vaginal insertion. The outer housing includes an upper portion that removably couples with a lower portion. A first inner vessel is located at the upper portion and is configured to house a first plurality of embryos. A second inner vessel is located at the lower portion and is configured to house a second plurality of embryos.

12 Claims, 9 Drawing Sheets

(56) References Cited

U.S. PATENT DOCUMENTS

| | | | |
|---|---|---|---|
| 5,681,742 A | 10/1997 | Merskelly | |
| 5,827,174 A | 10/1998 | Reuss, Jr. et al. | |
| 6,050,935 A | 4/2000 | Ranoux | |
| 7,282,363 B1 | 10/2007 | Ranoux et al. | |
| 7,759,115 B2 | 7/2010 | Etheredge | |
| 2004/0157205 A1 | 8/2004 | Etheredge, III | |
| 2010/0196871 A1* | 8/2010 | Dodgson | C12M 21/08 435/284.1 |
| 2011/0098731 A1* | 4/2011 | Whitbrook | A61F 2/0018 606/151 |
| 2016/0257918 A1* | 9/2016 | Chapman | C12M 21/06 |
| 2018/0014854 A1* | 1/2018 | Souther | A61B 17/43 |
| 2020/0015854 A1* | 1/2020 | Jacoby | A61B 17/425 |
| 2021/0145560 A1 | 5/2021 | Kahler et al. | |

OTHER PUBLICATIONS

Ranoux, C; Poirot, C.; Foulot, H.; Aubriot, FX; Dubuisson, JB; Chevallier, O.; Intravaginal culture and embryo transfer. Revue francaise de gynecologie et d'obstretrique, Oct. 1988; vol. 83 (10), pp. 637-638. English Abstract. Paris, France. ISSN: 0035-290X.

U.S. Appl. No. 62/938,154; IVC Container and Method; Kahler et al.; Applicant: INVO Bioscience, Inc.; filed Nov. 20, 2019.

U.S. Appl. No. 62/938,122; Improved Incubation and/or Storage Container System and Method; Kahler et al.; Applicant: INVO Bioscience, Inc.; filed Nov. 20, 2019.

English Machine Translation of RU2250757C2. Obtained on Feb. 23, 2022 from Espacenet.

* cited by examiner

GAS PERMEABLE INTRAVAGINAL CULTURE DEVICE

CROSS-REFERENCE TO RELATED APPLICATIONS

The present application claims the benefit of U.S. Provisional Application No. 63/108,817, filed September Nov. 2, 2020, the entire contents of which are expressly incorporated by reference.

TECHNICAL FIELD

The present application generally relates to assisted reproductive technologies, and more specifically, but not exclusively, to in vivo embryonic culture devices.

BACKGROUND

Assisted reproductive technologies, including in vitro fertilization (hereinafter "IVF"), are commonly utilized by those suffering infertility. Historically, embryos have been cultured in Petri dishes. The embryos housed in these Petri dishes are maintained in embryonic culture media, which is then overlaid with mineral oil. The Petri dishes are placed in laboratory incubators which maintain the temperature of the embryonic culture media and embryos. The incubators are set at 37° C., and the incubators are filled with a premixed gas comprising approximately 5% Oxygen and 7.5% Carbon Dioxide. This specific temperature and gas concentration enables an adequate pH of the culture media to be maintained, and is designed to simulate the in vivo conditions thought to be required for early embryonic development.

Attempts have been made to create an in vivo culture system that would allow human embryos to develop within the female body, specifically within the vaginal canal. The conditions inside the vaginal canal are similar to the natural environment for embryonic development (e.g. within the uterus). Intravaginal Culture (hereinafter "IVC") permits the embryos to develop in advanced contemporary culture media that supports embryo development to day 5, which is the blastocyst stage.

As IVC devices are housed within the patient's vagina, the embryos will develop at a temperature that is unique to that specific patient, and will be exposed to the normal temperature variations of the human body. Rather than culturing embryos statically in an IVF incubator in the lab, women with IVC devices are mobile for the entire 5 days of culture and development. The conditions to which the IVC devices are exposed mimic the in utero condition of embryonic development, rather than the static conditions of a laboratory incubator. The costs associated with IVC devices are typically less than traditional in incubator culturing. Additionally, there is an emotional component where a woman feels more involved with the development of their embryo(s) when the embryo cultures internal to her body, rather than in a laboratory.

U.S. Pat. No. 6,050,935 to Ranoux et al. and U.S. Pat. No. 7,759,115 to Etheredge, Ill et al. teach of exemplary IVC devices of the prior art. The product embodying the teachings of U.S. Pat. No. 7,759,115 is sold commercially under the trade name INVOCELL®. The INVOCELL® device is believed to be the only IVC device that is presently commercially available. At least one study has shown that embryo quality and pregnancy rates with the INVOCELL® device are equivalent to conventional IVF.

However, there are numerous drawbacks to the IVC devices of the prior art, including the INVOCELL® device. For the INVOCELL® device to function properly, a high $CO_2$ gas concentration is required in a buffer chamber. This buffer chamber substantially surrounds an inner vessel which contains the gametes/embryos and culture medium. The $CO_2$ enriched atmosphere contained in the buffer chamber diffuses through the wall of the inner vessel to maintain an adequate pH within the buffer chamber. The INVOCELL® device must be assembled in an IVF chamber to provide the high $CO_2$ atmosphere in the buffer chamber. The high economic cost of IVF chambers prevents many practitioners from having ready access to IVF chambers; therefore, few practitioners are able to utilize the INVOCELL® device. This high economic cost has proven prohibitive to the adoption of the INVOCELL® device in fertility clinics.

Moreover, the conical shape of the inner vessel of the INVOCELL® device places the embryos at great risk of wide temperature fluctuations when the device is removed from the vagina, prior to embryo removal for eventual embryo transfer. The human body temperature is 37° C., and the typical laboratory temperature is about 22-25° C. The temperature of the media and the embryos housed within the conical inner vessel will drop significantly within minutes due to large surface area provided by the conical shape of the inner vessel. Temperature is extremely important in oocyte/embryo culture and development.

In order to reduce the rapid heat loss when the embryos are removed, the INVOCELL® device utilizes a heating block. This heating block is warmed in an incubator for several hours prior to use, and is then placed on a microscope stage, with the inner vessel of the INVOCELL® device plugged into the side. Once inserted into the heating block, a lab technician can then look through a small opening to identify the gametes and/or embryos to be removed. This process is cumbersome and time consuming. The heating block adds economic cost to the use of the INVOCELL® device.

The INVOCELL® device includes a sealed, non-gas permeable outer container to prevent the egress of $CO_2$ from the buffer chamber into the vagina. An upper cap is utilized to seal the inner vessel of the INVOCELL® device. This cap includes a tiny hole that requires a small flexible pipette to be introduced in order to place or remove gametes or embryos. The embryos are typically found to be lodged into the far tip of the conical inner vessel, so the pipette has to bend in order to remove them easily. This is a very time consuming process, and embryos can be damaged.

The commercially available INVOCELL® device includes a seam along the bottom edge where the embryos tend to sit. When the embryos are removed toward day 5 of incubation, small portions of this ridged seam have been found to separate and appear as debris into the culture medium. This debris may be detrimental to the development of the embryos. In rare instances, this debris has been observed to puncture the embryos/oocytes.

Therefore, further technological developments are desirable.

SUMMARY

One form of the present application is directed to an intravaginal culture apparatus. This intravaginal culture apparatus includes an outer housing configured for vaginal insertion. The outer housing includes an upper portion and a lower portion. The upper portion removably couples with the lower portion.

A first inner vessel is located at the upper portion, and the first inner vessel is configured to house a first plurality of embryos. A second inner vessel is located at the lower portion, and the second inner vessel is configured to house a second plurality of embryos.

The first inner vessel can be removably received in the upper portion, and the second inner vessel can be removably received in the lower portion. The first inner vessel and the second inner vessel can each include a base and a removable lid configured to sealingly engage with the base. The lid can be formed of a polymer.

Preferably, the outer housing and the base are $CO_2$ permeable. The outer housing and the base can be formed of crystal polystyrene. The upper portion can removably couple with the lower portion through a threaded connection. The intravaginal culture apparatus is preferably devoid of a $CO_2$ enriched buffer chamber. As such, an IVF chamber is not required to load the intravaginal culture apparatus.

Another form of the present application is directed to an apparatus which includes an outer vessel configured for insertion into a vaginal canal. The outer vessel includes an upper portion configured to sealingly engage with a lower portion.

A first inner vessel defines a first receiving chamber, and the first inner vessel is removably received in the upper portion. A second inner vessel defines a second receiving chamber, and the second inner vessel is removably received in the lower portion. The first receiving chamber and the second receiving chamber are each configured to house a culture medium and at least one of a gamete and an embryo.

The outer vessel, the first inner vessel, and the second inner vessel preferably each include a gas permeable portion. The gas permeable portion permits the passage of $CO_2$ between the vaginal canal and the first receiving chamber, and permits the passage of $CO_2$ between the vaginal canal and the second receiving chamber. The outer vessel, the first inner vessel, and the second inner vessel are preferably formed of crystal polystyrene. Such a crystal polystyrene construction is $CO_2$ permeable, and can be transparent.

A first lid can be removably coupled to the first vessel to selectively provide access to the first receiving chamber. A second lid can be removably coupled to the second vessel to selectively provide access to the second receiving chamber. The first receiving chamber can include an internal fillet. Preferably, a base of the first inner vessel can be configured to be received in a well of a 4-well laboratory dish.

The upper portion can threadingly engage with the lower portion. An interference seal can be formed between the upper portion and the lower portion when in a closed configuration to prevent the ingress of vaginal liquids into the outer vessel when the outer vessel is in the closed configuration.

Yet another form of the present application is directed to an intravaginal culture apparatus which is devoid of a $CO_2$ enriched buffer chamber. This apparatus includes an outer container configured for insertion into a vaginal canal. A receiving cavity is located internal to the outer container. An inner vessel is removably received in the receiving cavity, and the inner vessel includes an interior chamber configured to house at least one of a gamete and an embryo.

The outer container and the inner vessel are preferably $CO_2$ permeable. The outer container can include an upper portion configured to sealingly engage with a lower portion. The receiving cavity can be located in the upper portion. A second receiving cavity can be located in the lower portion, and a second inner vessel can be removably received in the second receiving cavity.

The outer container, the inner vessel, and the second inner vessel can be constructed of polystyrene. The upper portion can engage with the lower portion through a threaded connection. The inner vessel and the second inner vessel can each include a removable lid.

Other embodiments include unique intravaginal culture apparatuses, systems, and methods. Further embodiments, inventions, forms, objects, features, advantages, aspects, and benefits of the present application are otherwise set forth or become apparent from the description and drawings included herein.

BRIEF DESCRIPTION OF THE DRAWING

The description herein makes reference to the accompanying drawings wherein like reference numerals refer to like parts throughout the several views, and wherein.

DETAILED DESCRIPTION

Figure 1:
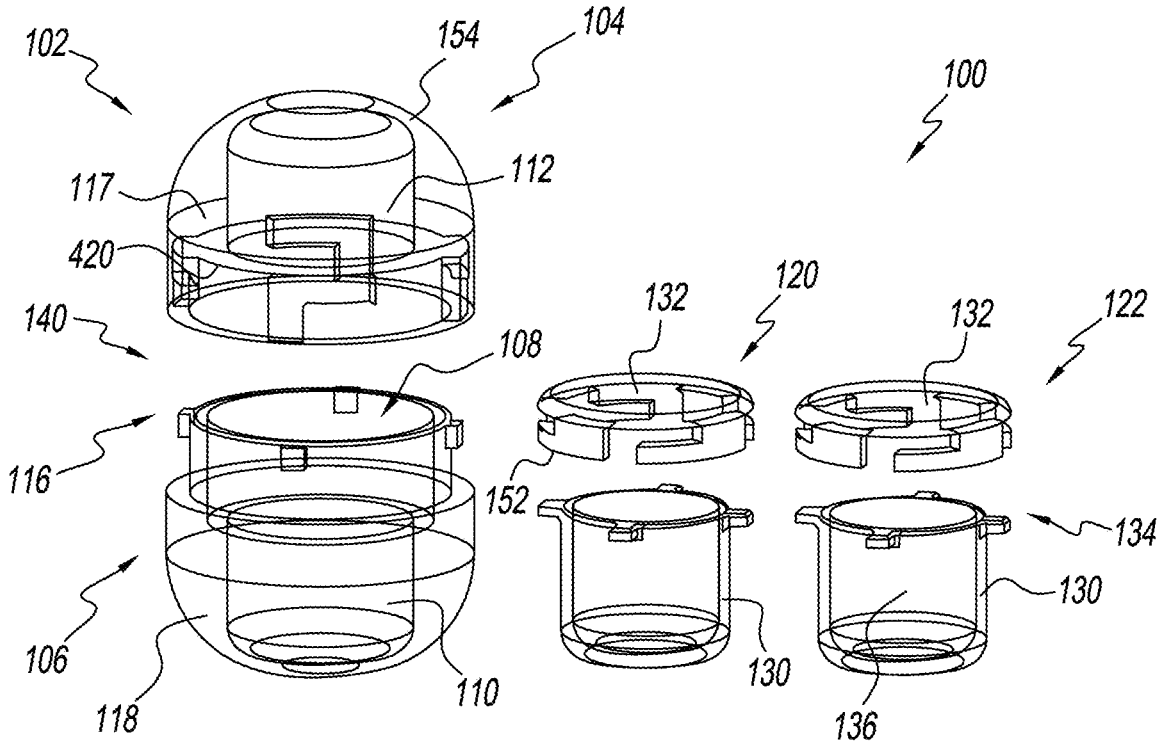
FIG. 1 is a perspective view of an intravaginal culture device according to a first form of the present application, which depicts an outer vessel, a first inner vessel, and a second inner vessel in an open configuration.
Figure 2:
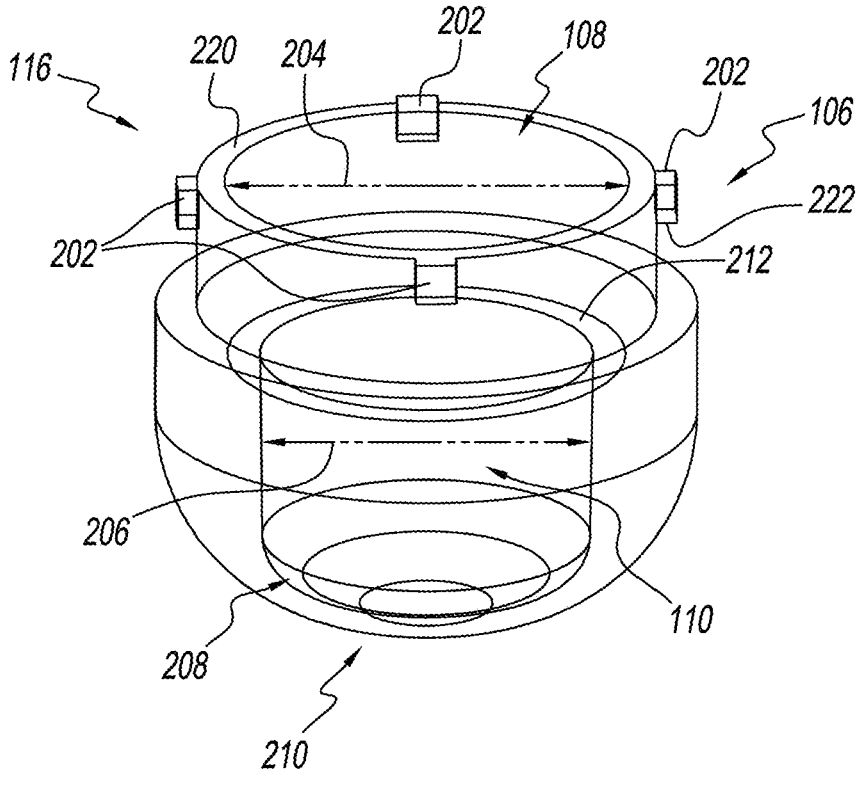
FIG. 2 is a perspective view of a lower portion of the outer vessel.
Figure 3:
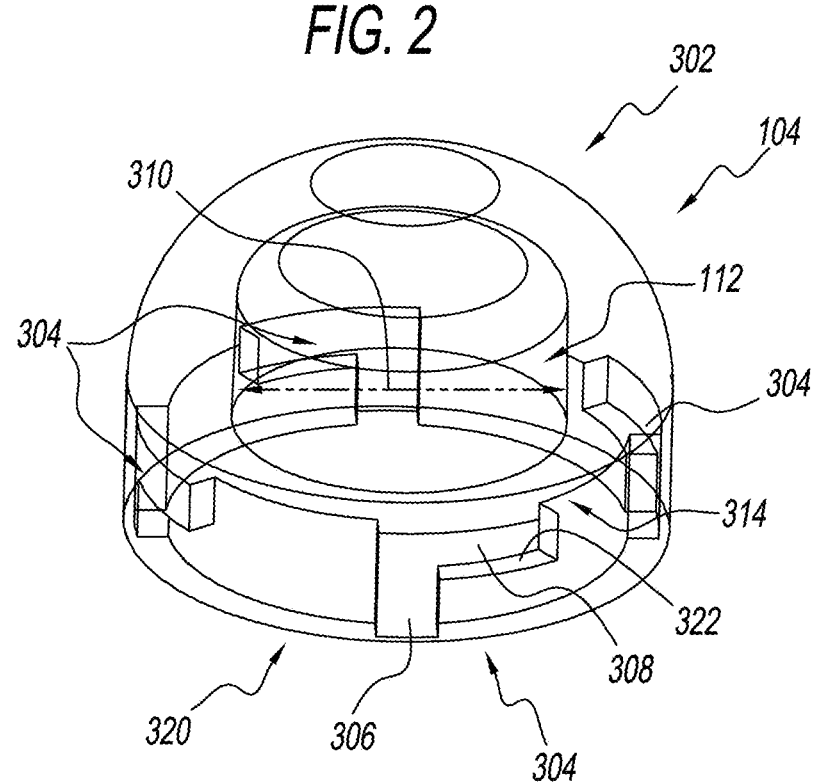
FIG. 3 is a perspective view of an upper portion of the outer vessel.

For purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated device, and any further applications of the principles of the invention as illustrated therein being contemplated as would normally occur to one skilled in the art to which the invention relates.

Referring now to FIGS. 1-4, an exemplary intravaginal culture device 100 will now be described. The intravaginal culture device 100 includes an outer vessel 102 and a first inner vessel 120. The first inner vessel 120 is removably contained within an interior cavity 108 of the outer vessel 102. The first inner vessel 120 is configured to house embryos and/or gametes and a suitable culture medium.

A second inner vessel 122 can also be contained within the interior cavity 108 of the outer vessel 102. The second inner vessel 122 is configured to house embryos and/or gametes, similar to the first inner vessel 120. It is contemplated that one or both of the first inner vessel 120 and the second inner vessel 122 can be inserted into the outer vessel 102, depending upon the specific application as well as the number of embryos and/or gametes to be cultured.

The outer vessel 102 will be inserted into the vaginal canal of a patient, and will be retained within the vaginal canal for the duration of the desired culture period. A typical culture period can approximate 5 days for embryonic development to the blastocyst stage; however, it is contemplated that the embryos and/or gametes can be cultured within the intravaginal culture device 100 for various durations to achieve the culture period desired by a fertility provider.

The outer vessel 102 includes an upper portion 104 and a lower portion 106. The upper portion 104 removably couples with the lower portion 106. The upper portion 104 is depicted as being selectively coupled to the lower portion 106 through a closure mechanism 140. In one preferred, non-limiting form the closure mechanism 140 is a twist-lock mechanism 116.

The twist-lock mechanism 116 includes tab engaging members 304 which cooperate with outwardly extending tabs 202. The tabs 202 extend outwardly from the lower portion 106. The tabs 202 are located near an upper rim 220 of the lower portion 106.

The upper portion 104 includes a plurality of tab engaging members 304. These tab engaging members 304 are located near a lower rim 320 of the upper portion 104. Each tab engaging member 304 includes a substantially vertically extending tab receiving opening 306 and a horizontally extending channel 308.

Figure 4:
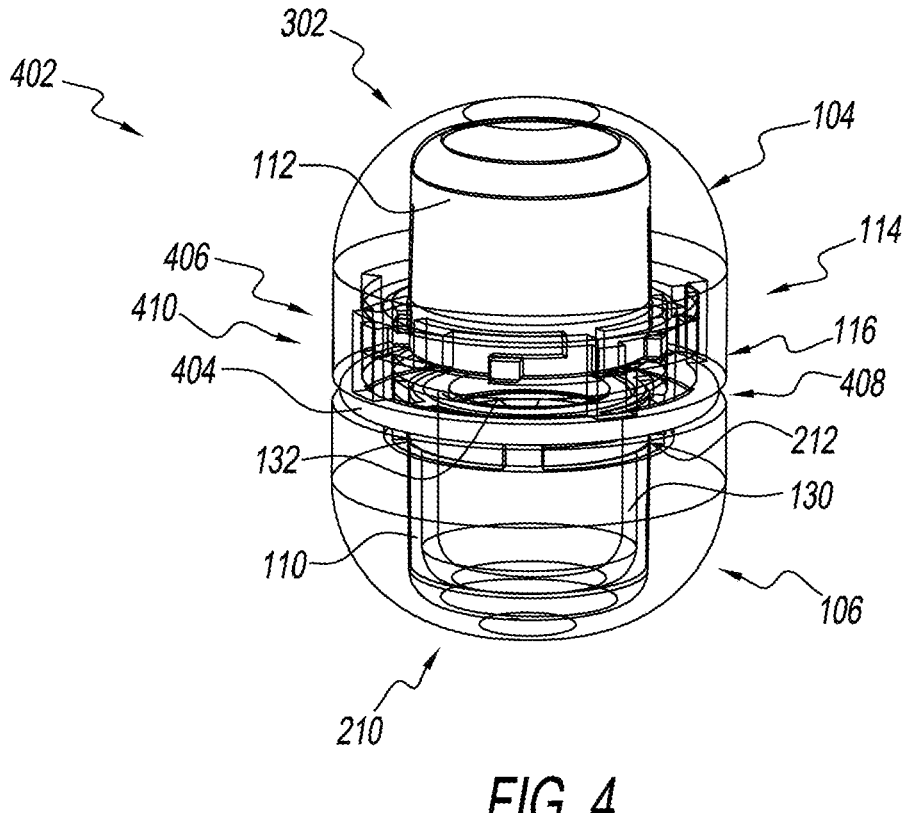
FIG. 4 is a perspective view of the intravaginal culture device of FIG. 1 in a configuration ready for vaginal insertion, which depicts a closed inner vessel housed in a lower portion of the closed outer vessel.

To close the outer vessel 102, each tab 202 of the lower portion 106 is aligned with and inserted into a vertically extending tab receiving opening 306 of the upper portion 104. Once the tabs 202 are fully inserted into the tab receiving openings 306, the upper portion 104 can then be rotated relative the lower portion 106, with the tabs 202 moving along the horizontally extending channels 308. Once the tabs 202 are located in the horizontally extending channels 308, a lower surface 222 of the tabs 202 abuts a lower surface 322 of the horizontally extending channels 308. This closed configuration 402 of the outer vessel 102 is depicted in FIG. 4.

The twist-lock mechanism 116 can additionally include an interference-type fit (not shown), or other locking-type mechanism, to further prevent the upper portion 104 from separating from the lower portion 106. In further forms, it is contemplated that the closure mechanism 116 can take the form of a press-lock mechanism, a screw-type threaded mechanism, or other closure mechanism 116 which can securely retain the upper portion 104 and lower portion 106 together.

A sealing member 404 can be located between the upper portion 104 and the lower portion 106. This sealing member 404 will contact the upper portion 104 and the lower portion 106 when the outer vessel 102 is in a closed configuration 402. The sealing member 404 prevents the ingress of liquids through an interface 408 between the upper portion 104 and the lower portion 106.

The sealing member 404 can take the form of a silicone O-ring; however, it is also contemplated that the sealing member 404 can be formed of a variety of biocompatible polymers, biocompatible rubbers, etc. to prevent the ingress of vaginal fluids through the interface 408. The sealing member 404 can be disposed at a variety of locations within the upper portion 104 and the lower portion 106 such that the sealing member 404 will contact both the upper portion 104 and the lower portion 106 when the outer vessel 102 is placed in a closed configuration 402. When in this closed configuration 402, the outer vessel 102 is a liquid sealed enclosure, which prevents the ingress of liquids (e.g. vaginal fluids) into the interior cavity 108.

As is illustrated in FIG. 4, the outer vessel 102 can take the form of a substantially spherocylindrical, capsule-type shape 114. The upper portion 104 can include a substantially hemispherical top 302, and the lower portion 106 can include a substantially hemispherical bottom 210. The mid-section 406 of the outer vessel 102 is depicted as having a cylindrical form 410. Although it is contemplated that the outer vessel 102 can take other forms, the hemispherical bottom 210 and hemispherical top 302 are believed to ease the insertion and the removal of the outer vessel 102 from the vaginal canal of a patient, and are believed to increase patient comfort during use.

Figure 5:
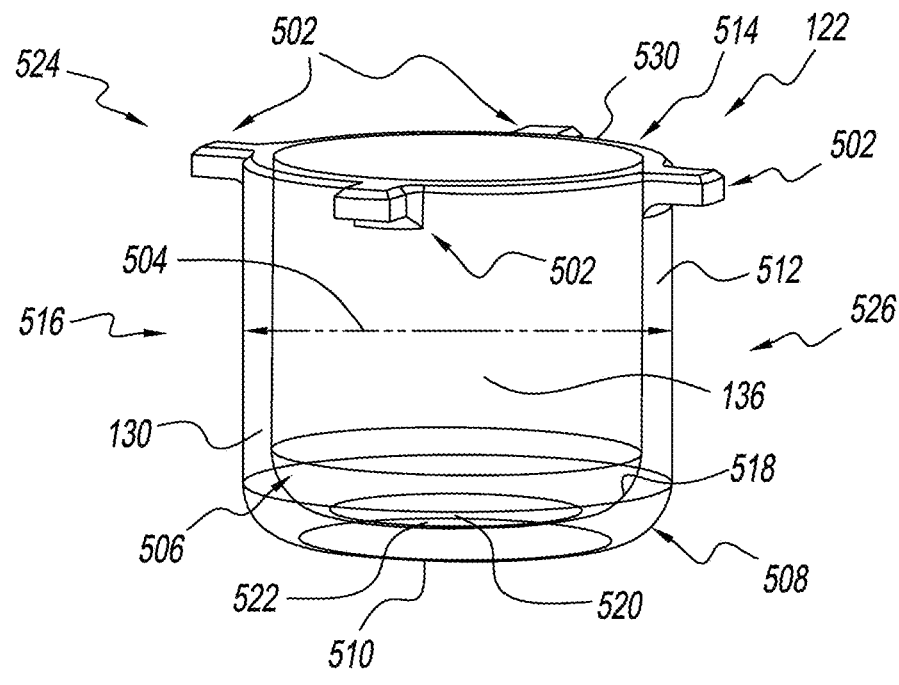
FIG. 5 is a perspective view of a base of the inner vessel.
Figure 6:
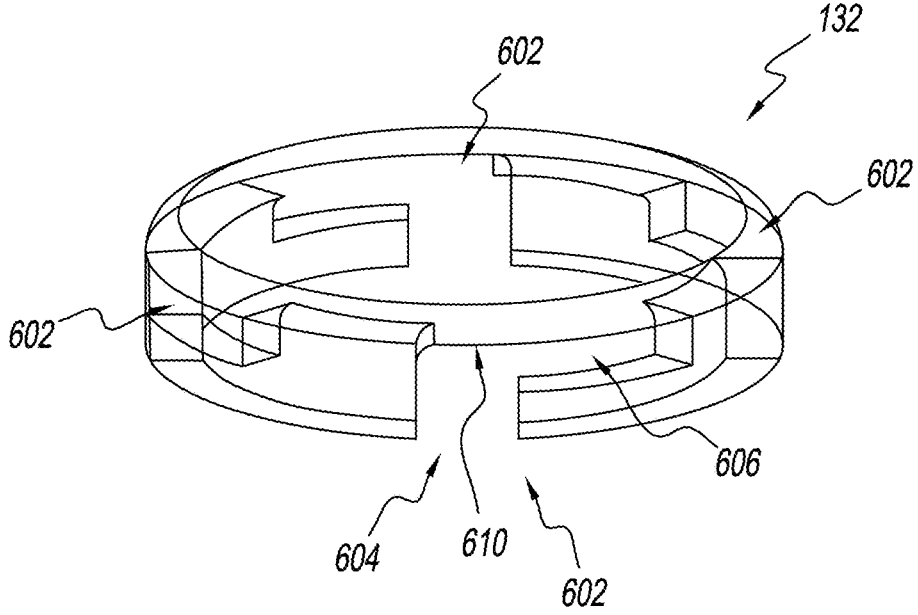
FIG. 6 is a perspective view of a lid that will sealingly engage with the base of FIG. 5.

Referring now to FIGS. 1 and 5, a first form of the first inner vessel 120 and the second inner vessel 122 will be described. The inner vessels 120 and 122 are each structured to contain embryos and/or gametes, as well as a suitable culture medium. In one non-limiting form, it is contemplated that each inner vessel 120, 122 can house between one and ten embryos. As is illustrated, the first inner vessel 120 and the second inner vessel 122 are preferably identical, and therefore interchangeable. As such, the inner vessel 122 will be described hereinafter, with inner vessel 120 including identical features.

The inner vessel 122 includes a base 130 which sealingly engages with a lid 132. The base 130 includes a sidewall 512 which extends between a closed lower portion 510 and an open upper portion 514. A receiving chamber 136 is accessed via the open upper portion 514. The base 130 can include a substantially cylindrical shape 516. The base 130 can include a rounded lower edge 508.

An inner lower edge 506 is located where the sidewall 512 abuts the closed lower portion 510. This inner lower edge 506 preferably includes a fillet 518. This fillet 518 directs the gametes and/or embryos stored within the receiving chamber 136 toward the center 520 of a lower surface 522 of the receiving chamber 136 when the base is placed in an upright orientation 524, as shown in FIG. 5. It is believed that this fillet 518 can ease the extraction of the gametes and/or embryos from the receiving chamber 136, as there is not a sharp transition for the gametes and/or embryos to be "trapped" in. The lower surface 522 of the receiving chamber 136 preferably includes a smooth design, which is free from any seams or other potentially sharp and/or debris introducing surfaces.

Referring now to FIGS. 1, and 5-7, the base 130 of the inner vessel 122 is sealingly closed with a lid 132. The lid 132 is removably coupled to the base 130 through a closure mechanism 134. This closure mechanism 134 is depicted as taking the form of a twist-lock mechanism 134. The twist-lock mechanism 134 takes a similar form as twist-lock mechanism 116.

The twist-lock mechanism 134 includes a plurality of outwardly extending tabs 502 and a plurality of tab engaging members 602. The outwardly extending tabs 502 are located near the upper portion 514 of the base 130. The tab engaging members 602 are located in the lid 132. Each tab engaging member 602 is depicted as including a vertically extending opening 604 and a horizontally extending channel 606.

To attach the lid 132 to the base 130, the tabs 502 are aligned with the openings 604 and the tabs 502 are pushed upwardly into the openings 604, as shown at 702. The lid 132 is then rotated with the tabs 502 cooperating with and extending along the horizontally extending channels 606. The inner vessel 122 is then in a fully closed configuration 704. In this closed configuration 704, the inner vessel 122 is a liquid sealed enclosure that confines the culture medium and embryos within the receiving chamber 136.

A sealing member (not shown) can be located at an interface of the base 130 and the lid 132. This sealing member can take the form of a silicone a-ring located on a lower surface 610 of the lid 132. In this manner, the sealing member will contact an upper rim 530 of the base 130 when the inner vessel 122 is in a closed configuration 704.

The sealing member (not shown) can alternatively be formed of a variety of biocompatible polymers, biocompatible rubbers, or the like. Alternatively, the sealing member can be located on the upper rim 530 of the base 130, or at any other suitable location whereby the sealing member will contact the base 130 and the lid 132 when the inner vessel 122 is in the closed configuration 704.

Referring back to FIGS. 1-5, the first inner vessel 120 can be housed in the upper portion 104 and the second inner vessel 122 can be housed in the lower portion 106. As was previously described, the first inner vessel 120 and the second inner vessel 122 are identical and interchangeable; therefore, the first inner vessel 120 can be housed in the lower portion 106 and the first inner vessel 120 can be housed in the upper portion 104. In this manner, a total of two internal vessels 120, 122 can be housed within the outer vessel 102.

The upper portion 104 of the outer vessel 102 includes a first receiving cavity 112. A second receiving cavity 110 is located within the lower portion 106. Each receiving cavity 110, 112 houses a lower portion 526 of an inner vessel 122 therein. As such, the internal diameters 310, 206 of the receiving cavities 112, 110 are slightly larger than an external diameter 504 of the base 130 of the inner vessels 120, 122. Each receiving cavity 112, 110 can include an internal fillet 208 configured to cooperate with the rounded lower edge 508 of the base 130.

The receiving cavity 110 of the lower portion 106 is depicted as including a lip 212. When the lower portion 526 of the inner vessel 122 is fully inserted into the receiving cavity 110, a lower rim 152 of the lid 132 can rest upon the lip 212. The receiving cavity 112 is depicted as including lip 420 upon which the lower rim 152 of the lid 132 of the inner vessel 120 can rest.

The lower portion 106 can include an enlarged inner diameter 204 located toward the rim 220. The inner diameter 204 is depicted as being larger than the diameter 206, to accommodate the lid 132 of the inner vessel 122. The upper portion 104 can also include an enlarged inner diameter located toward lower rim 320 to accommodate a lid 132.

In one preferable, non-limiting form, an external diameter 504 of the base 130 of the inner vessel 122 approximates an internal diameter of a 4-well dish, as are standard in IVF labs in the United States. The external diameter 504 of the base 130 is slightly less than 15 mm, 15 mm being the internal diameter of each well of the 4-well dish. Use of such a 4-well dish can enable ease of handling of the inner vessels 120, 122, and significantly reduces the likelihood of spillage from the inner vessels 120, 122.

Another potential advantage of having the base 130 fit into a 4-well dish is that such a configuration will have a flat bottom surface, which can then be placed upon a warmed microscope stage, as are common in IVF laboratories. The constant contact of the 4-well dish with the microscope stage will permit the transfer of heat from the microscope stage, through the 4-well dish, and into the base 130. It has been discovered that the ability to utilize a warmed microscope stage can eliminate the necessity to purchase a large metal heating block, as are commonly utilized with intravaginal culture devices of the prior art.

Referring back to FIG. 1, the upper portion 104 and the lower portion 106 of the outer vessel include a gas permeable portions 117, 118, respectively. These gas permeable portions 117, 118 permit the passage of $CO_2$ therethrough. Preferably, the upper portion 104 and the lower portion 106 are constructed of a gas permeable material 154, thereby providing a large surface area for $CO_2$ to permeate through. In one non-limiting form, the gas permeable material 154 is medical grade general purpose polystyrene GPPS; however, it is contemplated that other gas permeable polymers could also be utilized. The gas permeable material 154 enables the passage of $CO_2$ between the vaginal canal and the interior cavity 108 of the outer vessel 102.

Figure 7:
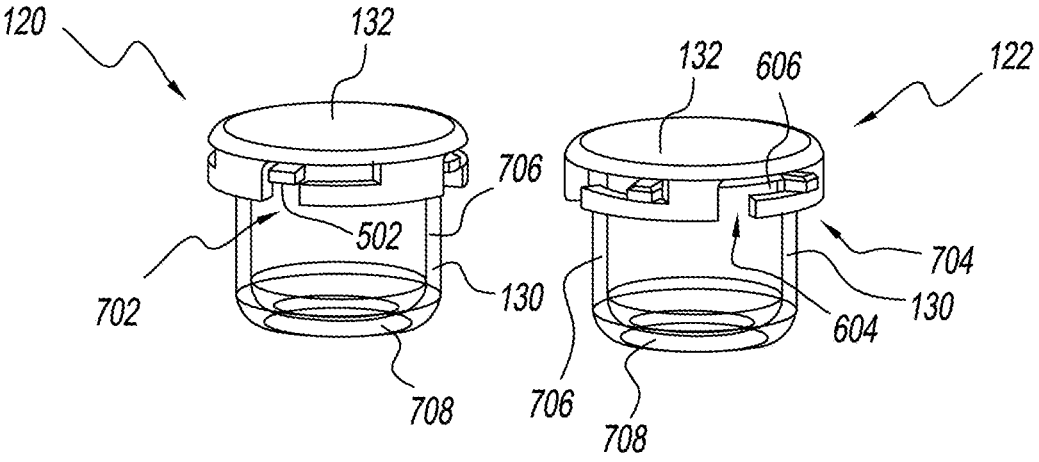
FIG. 7 is a perspective view depicting the closure of the inner vessel.

As shown in FIG. 7, the inner vessels 120, 122 include gas permeable portion 706. The gas permeable portion 706 enables the passage of $CO_2$ therethrough. Preferably, the base 130 can be constructed of a $CO_2$ gas permeable material 708. Such a construction provides a large surface area for $CO_2$ to permeate from the interior cavity 108 into and out of the receiving chamber 136. One exemplary gas permeable material 708 is medical grade general purpose polystyrene GPPS; however, the use of other $CO_2$ permeable polymers is contemplated herein.

The gas permeable portions 117, 118 and 706 enable the passage of $CO_2$ between the vaginal canal and the receiving chamber 136, in which the embryos and/or gametes are contained. The gas permeable construction of the outer vessel 102 and inner vessels 120, 122 permits passage of $CO_2$ between the vaginal canal and the receiving chamber 136. As such, a $CO_2$ concentration within the receiving chamber 136 will reach equilibrium with a $CO_2$ concentration of the vaginal canal, thereby subjecting the embryos and/or gametes housed within the receiving chamber 136 to the natural conditions of embryonic development.

Additionally, the free permeation of $CO_2$ between the receiving chamber 136 and the vaginal canal will regulate the pH of the culture medium contained within the receiving chamber 136. As is known to a person of skill in the art, the concentration of $CO_2$ present within the culture medium affects the pH of the culture medium. The free permeation of $CO_2$ between the receiving chamber 136 and the vagina will provide a suitable pH for embryonic development within the receiving chamber 136, assuming the vagina of the patient has a suitable pH for embryonic development.

It has been discovered that the $CO_2$ permeable construction of the outer vessel 102 and inner vessels 120, 122 eliminates the need for a $CO_2$ enriched buffer chamber from the intravaginal culture device 100 (e.g. the $CO_2$ in the enriched buffer chamber would merely permeate out of intravaginal culture device 100 into the vagina). As the intravaginal culture device 100 is devoid of a $CO_2$ enriched buffer chamber, a standard IVF incubator may be utilized to prepare the culture medium to be inserted into the present intravaginal culture device 100. This has been discovered to be highly advantageous as the present intravaginal culture device 100 does not require a costly IVF chamber to load.

Construction of the outer vessel 102 and inner vessels 120, 122 from general purpose polystyrene GPPS, which is a crystal polystyrene, can additionally be advantageous as such a construction can be transparent. The ability to see within the inner vessels 120, 122 without opening the lid 132 can reduce temperature fluctuations within the receiving chamber 136.

Figure 8:
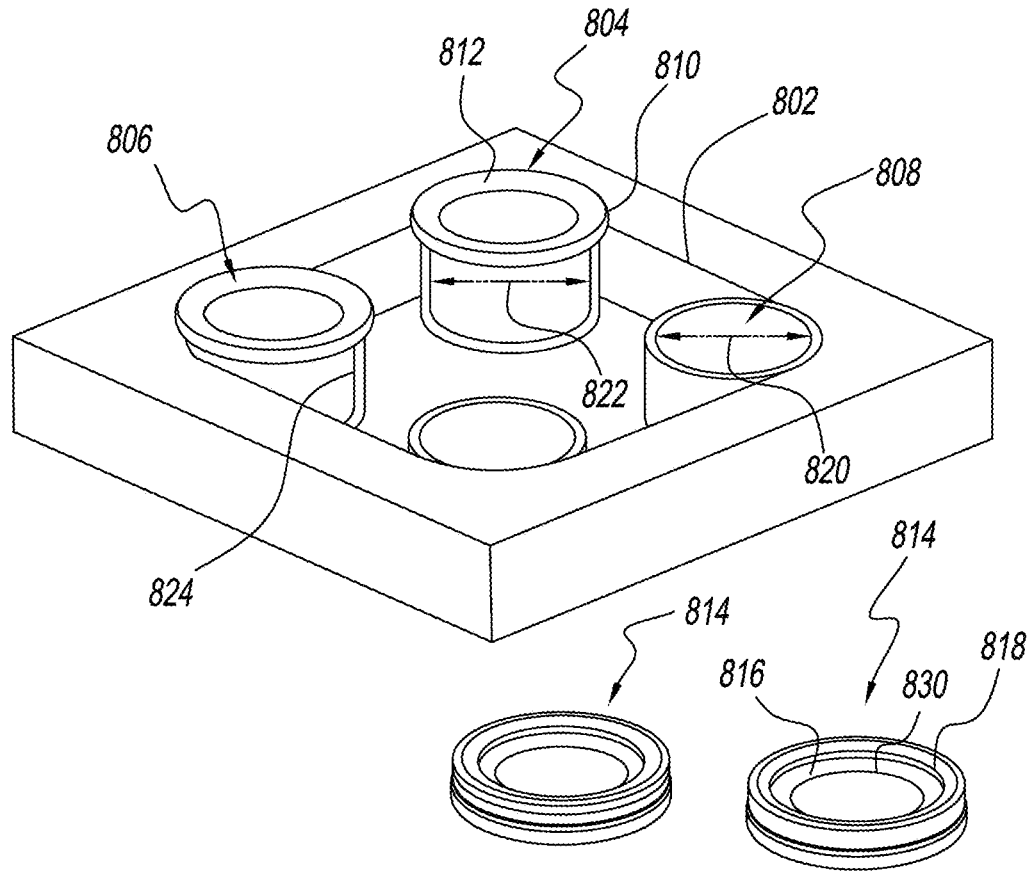
FIG. 8 is a perspective view of an alternative form of a first inner vessel and a second inner vessel which include press-fit lids, which depicts the first inner vessel and the second inner vessel located in wells of a 4-well IVF laboratory dish.

Referring now to FIG. 8, an alternative inner vessel 804, 806 construction will now be described. The inner vessels 804, 806 are depicted as being placed in a 4-well dish 802, as was previously described with inner vessels 120, 122. The inner vessels 804, 806 include a substantially cylindrical shape 824. The inner vessels 804, 806 can include an outer diameter 822 of approximately 15 mm, which is approximately the internal diameter 820 of each well 808 of the 4-well dish 802.

A primary difference between inner vessels 804, 806 and inner vessels 120, 122 is the closure mechanism. While inner vessels 120, 122 included a twist-lock closure mechanism 134, inner vessels 804, 806 are depicted as closing through a press-lock closure mechanism.

As inner vessels 804 and 806 are identical and interchangeable, only the closure mechanism of the first inner vessel 804 will be described. A base 812 of the inner vessel 804 is depicted as including an outwardly extending lip 810. A lid 814 includes an inwardly extending lip receiving channel 818. When the lid 814 is depressed onto the base 812, the outwardly extending lip 810 is forced into the lip receiving channel 818 which securely receives and retains the outwardly extending lip 810 therein, thereby removably coupling the lid 814 onto the base 812. A sealing member 816 can be located on an interior surface 830 of the lid 814 to sealingly contact with the base 812; thereby preventing the egress of culture medium from the inner vessel 804. However, it is also contemplated that the lid 814 can securely fasten to the base 812 through a threaded screw-on type closure mechanism.

Figure 9:
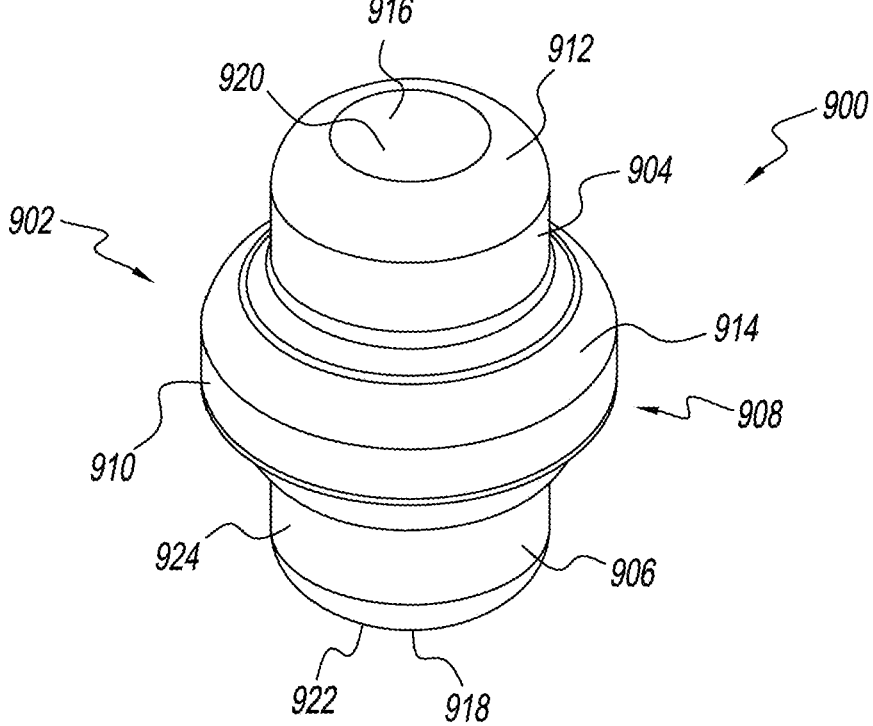
FIG. 9 is a perspective view of an intravaginal culture device according to another form of the present application, which depicts an outer container in a closed configuration.
Figure 10:
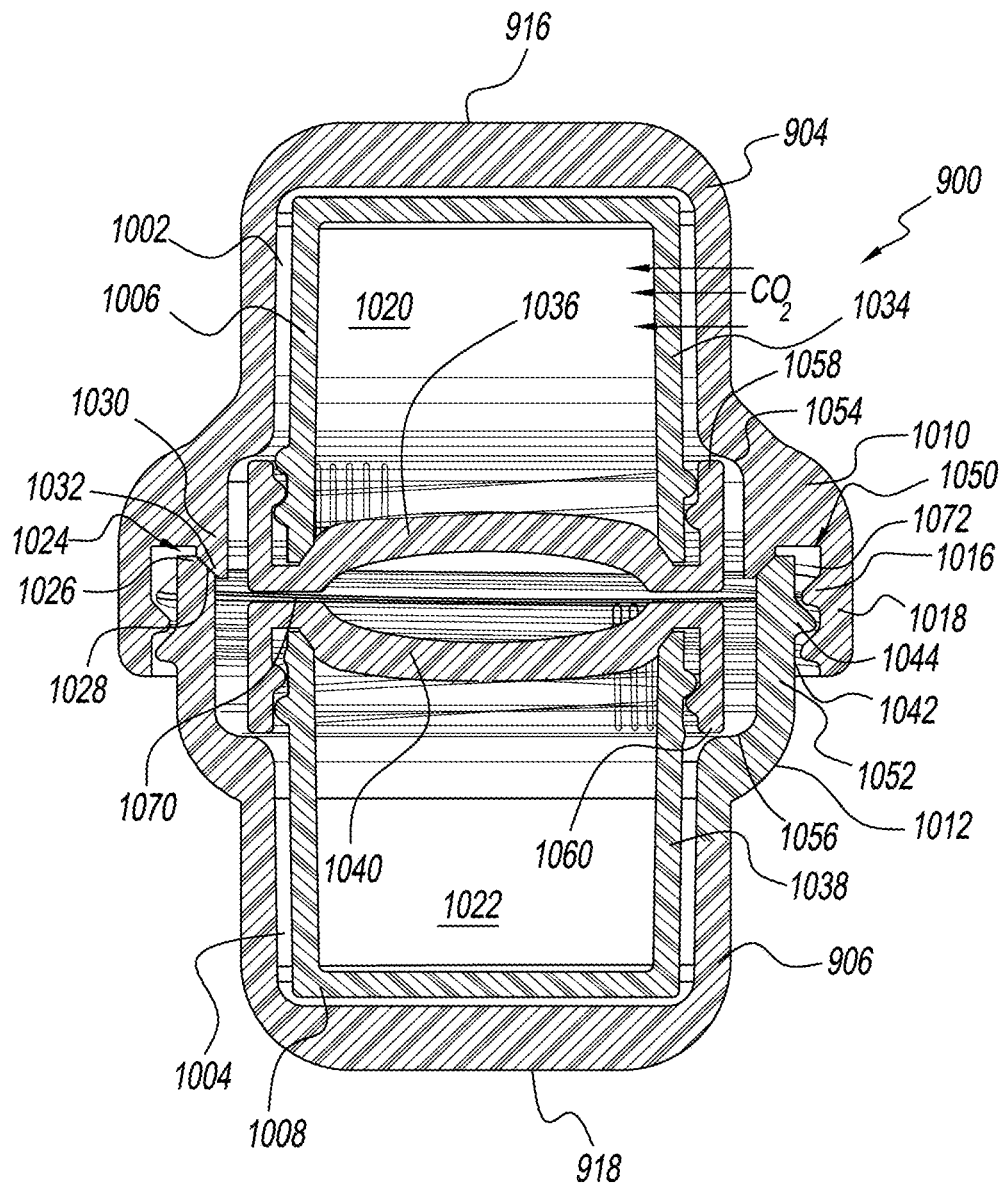
FIG. 10 is a sectional view of the intravaginal culture device of FIG. 9, which depicts a first inner vessel located in the upper portion and a second inner vessel located in the lower portion.
Figure 11:
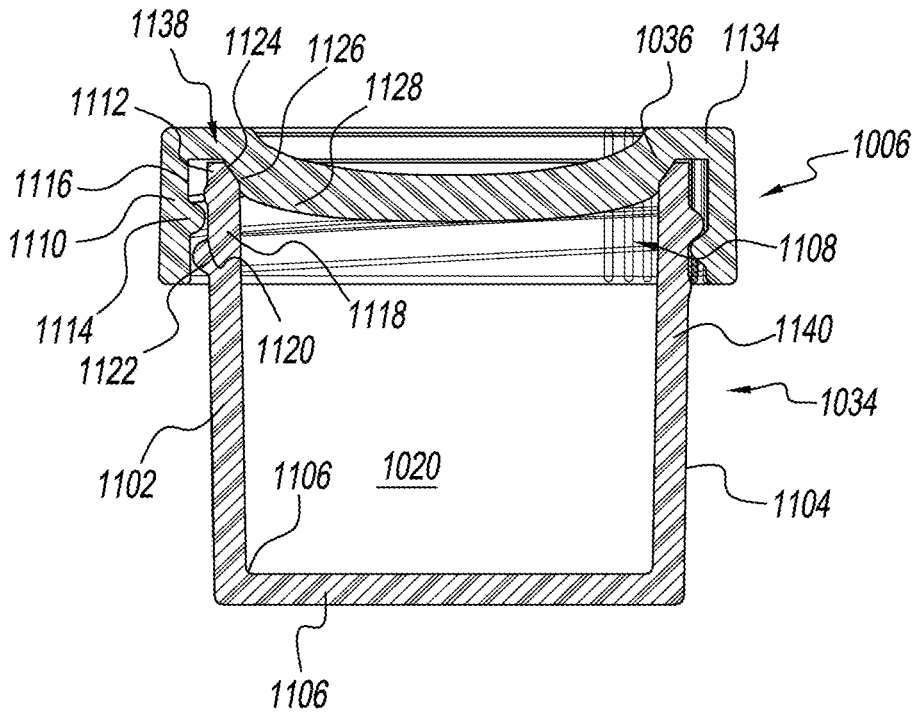
FIG. 11 is a sectional view of the first inner vessel in a closed configuration.

Referring now to FIGS. 9-11, another form of an intravaginal culture device 900 will now be described. The intravaginal culture device 900 includes an outer container 902. The outer container 902 includes an upper portion 904 and a lower portion 906. The upper portion 904 is configured to removably attach to the lower portion 906. The outer container 902 is depicted in a closed configuration 908 in FIG. 9, in which the upper portion 904 is securely attached to the lower portion 906.

The outer container 902 extends between an upper surface 920 and a lower surface 922. The upper surface 920 is depicted as including a flattened surface 916, and the lower surface 922 is depicted as including a flattened surface 918. The flattened surfaces 916 and 918 enable the outer container 902 to remain upright when placed on a flat surface, such as a laboratory table. When the upper portion 904 is detached from the lower portion 906, the upper portion 904 can be stood upright upon the flattened surface 916 and the lower portion 906 can be stood upright upon the flattened surface 918.

The outer container 902 is structured to be inserted into the vaginal canal of a patient, and will remain in the vaginal for a period of several days. To provide for ease of insertion and to maximize patient comfort, the outer container 902 is devoid of sharp edges. Transitional areas 912 and 914 of the outer container 902 are rounded and smooth. Portions 924 of the outer container 902 can have a substantially cylindrical form.

FIG. 10 depicts a sectional view of the intravaginal culture device 900. The upper portion 904 is removably attached to the lower portion 906 through a threaded connection 1050. As is illustrated, the upper portion 904 of the outer container 902 includes an outward flare 1010. A vertically oriented sidewall 1018 extends downwardly from the outward flare 1010. An inner surface 1072 of the vertically oriented sidewall 1018 includes internal threads 1016.

The lower portion 906 of the outer container 902 is depicted as including an outward flare 1012. A vertically oriented sidewall 1052 extends upwardly from the outward flare 1012. An outer surface 1042 of the vertically oriented sidewall 1052 includes external threads 1044.

The external threads 1044 of the lower portion 906 threadingly engage with the internal threads 1016 of the upper portion 904 to removably couple the upper portion 904 and the lower portion 906. To close the outer container 902, the external threads 1044 are aligned with the internal threads 1016 and the lower portion 906 is rotated relative the upper portion 904, thereby screwing the lower portion 906 into the upper portion 904.

The upper portion 904 sealingly engages with the lower portion 906 to prevent the ingress of liquids therein. An interference seal 1024 can be formed between the upper portion 904 and the lower portion 906. This interference seal 1024 is a sealing engagement between the upper portion 904 and the lower portion 906 in which the material of the upper portion 904 is firmly pressed against the material of the lower portion 906 in a manner sufficient to prevent the passage of liquids therethrough.

An exemplary interference seal 1024 will now be described. The upper portion 904 includes a downward extension 1030 which is located radially inward from the sidewall 1018. This downward extension 1030 includes an outward taper 1032. The vertically oriented sidewall 1052 of the lower portion 906 extends to an upper lip 1026. An inward taper 1028 extends downwardly from the upper lip 1026. When the lower portion 906 is screwed into the upper portion 904, the outward taper 1032 is firmly pressed against inward taper 1028 and in interference seal 1024 is formed therebetween, which prevents the ingress of vaginal liquids into the outer container 902.

Similar to the intravaginal culture device 100, the outer container 902 of the intravaginal culture device 900 houses a first inner vessel 1006 and a second inner vessel 1008. The first inner vessel 1006 is depicted as being located within the upper portion 904, and the second inner vessel 1008 is depicted as being located within the lower portion 906.

A first receiving cavity 1002 is located in the upper portion 904. A second receiving cavity 1004 is located in the lower portion 906. A base 1034 of the first inner vessel 1006 is removably positioned into the receiving cavity 1002 in the upper portion 904. A base 1038 of the second inner vessel 1008 is removably positioned into the receiving cavity 1004 of the lower portion 906. When the upper portion 904 is unscrewed from the lower portion 906, the inner vessels 1006 and 1008 can be completely removed from the outer container 902. The receiving cavities 1002, 1004 are depicted as taking a substantially cylindrical form. The bases 1034, 1038 of the inner vessels 1006, 1008 are closely received within, and substantially fill, the receiving cavities 1002, 1004.

The first inner vessel 1006 is preferably identical to the second inner vessel 1008, and includes similar features thereto. The first inner vessel 1006 includes a base 1034 and a lid 1036. An interior chamber 1020 is defined within the first inner vessel 1006. The second inner vessel 1008 includes a base 1038 and a lid 1040. An interior chamber 1022 is defined within the second inner vessel 1008.

When the outer container 902 is placed in a closed configuration 908, the lid 1036 of the first inner vessel 1006 may contact the lid 1040 of the second inner vessel 1008 as is shown at 1070. The outward flare 1010 of the upper portion 904 can be located radially outwardly from the lid 1036 to provide clearance for the lid 1036. The outward flare 1012 of the lower portion 906 can be located radially outwardly from the lid 1040 to provide clearance for the lid 1040. A lower rim 1058 of the lid 1036 may contact an inner surface 1054 of the flare 1010 of the upper portion 904. A lower rim 1060 of the lid 1040 may contact an inner surface 1056 of the flare 1012 of the lower portion 906.

The first inner vessel 1006 and the second inner vessel 1008 each enclose and contain gametes and/or embryos and a suitable culture medium. In one non-limiting form, each inner vessel 1006, 1008 can house between one and ten embryos (e.g. up to twenty embryos can be housed in the intravaginal culture device 900). However, it is also contemplated that the sizing of the inner vessels 1006, 1008 and the outer container 902 can be increased or decreased depending upon the specific application and number of embryos desired to be housed therein.

Referring now to FIG. 11, the first inner vessel 1006 will now be described. As was previously discussed, the second inner vessel 1008 is preferably identical to the first inner vessel 1006. The base 1034 of the first inner vessel 1006 includes a sidewall 1140 which extends upwardly from a closed lower portion 1106. The base 1034 includes an open top 1108. The base 1034 is depicted as taking a cylindrical form 1104, and the base 1034 is preferably sized to fit within a well of a 4-well IVF laboratory dish.

A lid 1036 threadingly engages with the base 1034 to close the open top 1108, thereby sealing the culture medium and embryos within the interior chamber 1020. An outer surface 1120 of the sidewall 1140 includes threads 1122. These threads 1122 are located near an upper portion 1118 of the base 1034. The lid 1036 includes a downwardly extending wall 1110. An inner surface 1116 of the downwardly extending wall 1110 includes threads 1114. The threads 1122 of the base 1034 cooperate with the threads 1114 of the lid 1036 to rotatably attach the lid 1036 to the base 1034. To close the first inner vessel 1006, the lid 1036 is rotated relative the base 1034 and the lid 1036 is screwed onto the base 1034.

An interference seal 1138 can be created between the base 1034 and the lid 1036. An inner surface 1126 of the lid 1036 includes a curvature 1128. An upper rim 1112 of the sidewall 1018 can include a curvature 1124 which is configured to abut the curvature 1128. When the lid 1036 is firmly screwed onto the base 1034, the curvature 1128 abuts the curvature 1124, and the material 1134 of the lid 1036 presses against the material 1102 of the base 1034 creating interference seal 1138. This interference seal 1138 prevents the egress of the culture medium and embryos from within the interior chamber 1020 of the inner vessel 1006.

Preferably, the outer container 902 is formed of a $CO_2$ permeable material 910. The inner vessels 1006 and 1008 are preferably formed of a $CO_2$ permeable material 1102. The materials 910 and 1102 can be medical grade general purpose polystyrene, which is commonly referred to as GPPS; however, the use of other $CO_2$ permeable polymers is also contemplated herein. GPPS is a crystal polystyrene which has insulative properties and can be transparent in nature. The ability to view inside the inner chambers 1020, 1022 without removing the lids 1036, 1040 can be beneficial as removal of the lids 1036, 1040 can cause the temperature within the inner chambers 1020, 1022 to fluctuate.

The lids 1036 and 1040 can be constructed of a polymeric material 1134. The lids can be formed of a $CO_2$ permeable material 1134, such as GPPS. However, the lids 1036 and 1040 can also be formed of polyethylene, thermoplastic elastomers, or other polymers.

The polystyrene construction of the outer container 902 and the bases 1034, 1038 permits $CO_2$ to pass between the vaginal cavity and the interior chambers 1020, 1022, but prevents the passage of liquids therethrough. As such, the outer container 902 prevents the ingress of vaginal fluids therein. The inner vessels 1006, 1008 prevent the egress of the culture medium fluid such that the culture medium fluid and embryos are confined within the interior chambers 1020, 1022. It is believed that the polystyrene construction of the outer container 902 and the bases 1034, 1038 will also serve as an insulator, thereby reducing temperature fluctuations with the embryos and/or gametes confined within the interior chambers 1020, 1022.

The passage of $CO_2$ between the vaginal canal and the interior chambers 1020, 1022, combined with a culture medium having a high initial $CO_2$ concentration (e.g. as can be achieved by leaving culture medium in a typical IVF lab incubator), has been discovered to sufficiently regulate the pH of the culture medium and thereby provide a suitable environment for the embryos and/or gametes. The intravaginal culture device 900 is devoid of a $CO_2$ enriched buffer chamber (i.e. a $CO_2$ enriched buffer chamber is absent from the intravaginal culture device 900). An IVF chamber is not required to load the intravaginal culture device 900.

One exemplary, non-limiting method of use of the intravaginal culture device 900 will now be described. On the day prior to oocyte retrieval, the intravaginal culture device 900 can be removed from its packaging and placed in an IVF lab incubator at 37° C., 7.5% CO2 to warm overnight. 1 ml of culture media and 1.5 ml of oil can be placed in a 37° C. triple gas IVF lab incubator to pre-equilibrate overnight.

On the day of oocyte retrieval, ICSI can be performed on the oocytes. The inner vessels 1006, 1008 can be removed from the IVF lab incubator and placed into a warmed 4-well dish on a heated microscope stage to be prepared. The lids 1036, 1040 are removed from the bases 1034, 1038 of the inner vessels 1006, 1008. The interior chambers 1020, 1022 of the inner vessels 1006, 1008 can each be filled with 500 ul culture media with a 500 ul oil overlay.

The injected oocytes (e.g. fertilized oocytes) can then be loaded into the interior chambers 1020, 1022 of the inner vessels 1020, 1022. As was previously discussed, it is contemplated that up to 10 embryos can be inserted into each inner vessel 1020, 1022, and a total of 20 embryos can be housed within the intravaginal culture device 900. After the oocytes are placed in the interior chambers 1020, 1022, the lids 1036, 1040 can be screwed onto the bases 1034, 1038 sealing the embryos and culture media within the interior chambers 1020, 1022.

The outer container 902 can be removed from the IVF lab incubator and unscrewed, separating the upper portion 904 from the lower portion 906. The first inner vessel 1006 is placed in the upper portion 904 and the second inner vessel 1008 is placed in the lower portion 906. With the inner vessels 1006, 1008 in place, the lower portion 906 is screwed into the upper portion 904, thereby sealing the outer container 902.

The loaded intravaginal culture device 900 can then be placed into the 37° C., 7.5% CO2 IVF lab incubator until the patient is ready for device placement. The intravaginal culture device 900 can be removed from the IVF lab incubator to be inserted into the upper vaginal canal of the patient. Depending upon the specific patient, or upon the preferences of the fertility provider, a diaphragm (not shown) may be inserted into the vaginal canal below the intravaginal culture device 900 to securely retain the intravaginal culture device 900 in the upper vaginal canal.

The intravaginal culture device 900 can remain in the upper vaginal canal of the patient for a predetermined time, such as 5 days to the blastocyst stage. After the predetermined time, the patient can return to the fertility provider. The fertility provider can remove the intravaginal culture device 900 from the vaginal canal of the patient. Once removed from the patient, the upper portion 904 can be unscrewed from the lower portion 906. The inner vessels 1006, 1008 are then removed from the outer container 902. The inner vessels 1006, 1008 can then be placed into a pre-warmed 4-well dish, which can be placed onto a heated microscope stage. The lids 1036, 1044 can be unscrewed from the bases 1034, 1038, and the embryos can be removed from the interior chambers 1020, 1022 to then be evaluated, graded, and eventually transferred, biopsied, or cryopreserved.

Referring now to both intravaginal culture devices 100 and 900, the intravaginal culture devices 100, 900 can be individually packaged, and can be sterilized by gamma irradiation. It is also contemplated that the intravaginal culture devices 100, 900 can be single use devices; therefore, all components can be discarded after any embryos and/or gametes have been removed.

The intravaginal culture devices 100 and 900 can be manufactured through injection molding; however, other construction techniques such as milling and vacuum forming are contemplated herein. It is contemplated that metallic inserts (not shown) can be integrated into the devices 100, 900 during the molding process for added strength. For example, it may be desirable to utilize metallic inserts for the tabs 202 in the intravaginal culture device 100, and may be desirable to utilize metallic inserts for the threads 1016, 1044, 1114, and 1122 in the intravaginal culture device 900.

It is also contemplated that the tabs 202 can be integrally formed with the base 130 from polystyrene. The threads 1016 can be integrally formed or machined in the upper portion 904 from polystyrene, and the threads 1044 can be integrally formed or machined in the lower portion 906 from polystyrene. The threads 1122 can be integrally formed or machined in the base 1034 from polystyrene.

The intravaginal culture devices 100, 900 have been described with regard to assisting with human reproduction. However, it is also contemplated that the intravaginal culture devices 100, 900 can be utilized to assist with equine, bovine, or swine reproduction with equal effect.

While the invention has been described in connection with what is presently considered to be the most practical and preferred embodiment, it is to be understood that the invention is not to be limited to the disclosed embodiment (s), but on the contrary, is intended to cover various modifications and equivalent arrangements included within the spirit and scope of the appended claims, which scope is to be accorded the broadest interpretation so as to encompass all such modifications and equivalent structures as permitted under the law.

It should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. An intravaginal culture apparatus, comprising:
an outer housing configured for vaginal insertion, wherein the outer housing includes an upper portion and a lower portion, and wherein the upper portion removably couples with the lower portion;
a first inner vessel located at the upper portion, wherein the first inner vessel is configured to house a first plurality of embryos;
a second inner vessel located at the lower portion, wherein the second inner vessel is configured to house a second plurality of embryos;
wherein the first inner vessel and the second inner vessel each include a base and a removable lid configured to sealingly engage with the respective base; and
wherein the outer housing, the first inner vessel base and the second inner vessel base are $CO_2$ (carbon dioxide) permeable.

2. The intravaginal culture apparatus of claim 1, wherein the first inner vessel is removably received in the upper portion, and wherein the second inner vessel is removably received in the lower portion.

3. The intravaginal culture apparatus of claim 1, wherein the outer housing and the first inner vessel base and the second inner vessel base are formed of crystal polystyrene.

4. The intravaginal culture apparatus of claim 3, wherein the first inner vessel lid and the second inner vessel lid are formed of a polymer.

5. The intravaginal culture apparatus of claim 1, wherein the upper portion removably couples with the lower portion through a threaded connection.

6. The intravaginal culture apparatus of claim 1, wherein the intravaginal culture apparatus is devoid of a $CO_2$ enriched buffer chamber.

7. An apparatus, comprising:
an outer vessel configured for insertion into a vaginal canal, wherein the outer vessel includes an upper portion configured to sealingly engage with a lower portion;
a first inner vessel defining a first receiving chamber, wherein the first inner vessel is removably received in the upper portion;
a second inner vessel defining a second receiving chamber, wherein the second inner vessel is removably received in the lower portion;
a first lid removably coupled to the first inner vessel;
a second lid removably coupled to the second inner vessel;
wherein the first receiving chamber and the second receiving chamber are each configured to house a culture medium and at least one of a gamete and an embryo; and
wherein the outer vessel, the first inner vessel, and the second inner vessel each include a gas permeable portion configured to permit the passage of $CO_2$ between the vaginal canal and the first and the second receiving chambers.

8. The apparatus of claim 7, wherein the outer vessel, the first inner vessel, and the second inner vessel are formed of crystal polystyrene.

9. The apparatus of claim 7, wherein the first lid is configured to selectively provide access to the first receiving chamber; and wherein the second lid is configured to selectively provide access to the second receiving chamber.

10. The apparatus of claim 7, wherein the first receiving chamber further includes an internal fillet.

11. The apparatus of claim 7, wherein a base of the first inner vessel is configured to be received in a well of a 4-well laboratory dish.

12. The apparatus of claim 7, wherein the upper portion threadingly engages with the lower portion, wherein an interference seal is formed between the upper portion and the lower portion while in a closed configuration, and wherein the outer vessel is configured to prevent the ingress of vaginal liquids while in the closed configuration.

* * * * *